United States Patent [19]

Nuber et al.

[11] Patent Number: 4,767,613
[45] Date of Patent: Aug. 30, 1988

[54] TERPOLYMERS, THEIR USE IN HAIR TREATMENT AGENTS AND HAIR TREATMENT AGENTS CONTAINING THESE TERPOLYMERS

[75] Inventors: Adolf Nuber, Boehl-Iggelheim; Axel Sanner, Frankenthal; Ferdinand Straub, Hockenheim; Friedrich Vogel, Wachenheim, all of Fed. Rep. of Germany

[73] Assignee: BASF Aktiengesellschaft, Rheinland-Pfalz, Fed. Rep. of Germany

[21] Appl. No.: 76,874

[22] Filed: Jul. 23, 1987

[30] Foreign Application Priority Data

Aug. 18, 1986 [DE] Fed. Rep. of Germany ....... 3627970

[51] Int. Cl.[4] .......................... B05D 3/14; C08F 26/08
[52] U.S. Cl. .......................................... 424/47; 424/71; 424/DIG. 1; 524/548; 525/326.9; 526/264
[58] Field of Search .................... 526/264; 424/47, 71, 424/DIG. 1; 524/548; 525/326.9

[56] References Cited

U.S. PATENT DOCUMENTS

| | | | |
|---|---|---|---|
| 2,996,471 | 8/1961 | Reiter et al. | 524/555 |
| 3,222,329 | 12/1965 | Grosser et al. | 526/264 |
| 3,405,084 | 10/1968 | Bohac et al. | 424/47 |
| 3,577,517 | 5/1971 | Kubot et al. | 424/47 |
| 3,910,862 | 10/1975 | Barabas et al. | 525/353 |
| 4,283,384 | 8/1981 | Jacquet et al. | 424/61 |
| 4,366,099 | 12/1982 | Gaetani et al. | 525/279 |

FOREIGN PATENT DOCUMENTS

995283 6/1965 United Kingdom ................ 526/264

*Primary Examiner*—Joseph L. Schofer
*Assistant Examiner*—N. Sarafim
*Attorney, Agent, or Firm*—Oblon, Fisher, Spivak, McClelland & Maier

[57] ABSTRACT

A terpolymer of vinylpyrolidone, tert-butyl (meth)acrylate and acrylic or methacrylic acid, its use in hair treatment agents, and hair cosmetics compositions which contain these agents.

5 Claims, No Drawings

TERPOLYMERS, THEIR USE IN HAIR TREATMENT AGENTS AND HAIR TREATMENT AGENTS CONTAINING THESE TERPOLYMERS

The present invention relates to a terpolymer of vinylpyrrolidone, tert-butyl (meth)acrylate and acrylic or methacrylic acid, its use in hair treatment agents, and compositions for the hair cosmetics sector which contain these terpolymers.

Film-forming resins based on carboxyl-containing vinylmonomers and (meth)acrylates and/or vinyl acetate have long been used, particularly for hair sprays in which halohydrocarbons, such as fluorohydrocarbons, are used as propellants. For practical use, it is advantageous to neutralize some or all of the carboxyl groups, for example with an amine or an aminohydroxy compound, as described in U.S. Pat. Nos. 2,996,471, 3,405,084 or 3,577,517. The partial or complete neutralization improves the water solubility or dispersability of the resin used and makes them easier to remove from the hair during washing. Neutralization makes it possible to have an advantageous effect on the flexibility of the films sprayed on.

For ecological reasons, the halohydrocarbons in aerosol hair spray formulations are increasingly being replaced with pure hydrocarbons, such as propane or butane. The use of these hydrocarbons as propellants gives rise to a number of problems, the reduced solubility of the hair spray resins, for example in alcoholic solution in the presence of these hydrocarbons as propellants, playing a particular role. Although the carboxylated resins are as a rule readily soluble in anhydrous alcohol/halohydrocarbon spray formulations, their reduced solubility in the alcohol/hydrocarbon formulations which have recently come into use may make them unacceptable for modern hair spray formulations.

U.S. Pat. No. 3,405,084 describes neutralized terpolymers for hair spray formulations which consist of from 20 to 75% by weight of vinylpyrrolidone, from 20 to 70% by weight of an alkyl ester of acrylic or methacrylic acid, where the ester alcohol has a saturated straight-chain or branched radical of 1 to 10 carbon atoms, and from 3 to 25% by weight of acrylic acid or methacrylic acid.

The description mentions propyl, isopropyl, butyl and isobutyl acrylates and methacrylates as examples of copolymerized acrylates and methacrylates, and the examples described terpolymers obtained from ethyl methacrylate, ethyl acrylate, butyl methacrylate, hexyl methacrylate and butyl acrylate.

The disadvantage of these terpolymers actually described in U.S. Pat. No. 3,405,084 when used in practice, especially in hair sprays, is that some of them have unsatisfactory, insufficient solubility in the propellant gases, such as propane, butane, isopentane or mixtures of these, which are preferred today for ecological reasons, although this prior art (column 7, line 49) also mentions hydrocarbons as propellants in a general way. Other terpolymers of this type which have been described and have sufficiently high solubility have the disadvantage that they tend to become tacky, making them unsuitable for use in cosmetics, and possess insufficient curl retention.

It is an object of the present invention to provide terpolymers where the abovementioned difficulties in relation to solubility in hydrocarbon propellants and in aerosol formulations, improved curl retention and the formation of non-tacky films on the air can be overcome.

We have found that this object is achieved by a terpolymer which is obtained by free radical polymerization of from 20 to 50% by weight of vinylpyrrolidone, from 40 to 70% by weight of tert-butyl acrylate or tert-butyl methacrylate and from 2 to 15% by weight of acrylic acid or methacrylic acid and, if necessary, from 5 to 100%, preferably from 50 to 90%, of whose carboxyl groups have been neutralized by an organic amine, and which has a K value of from 10 to 60.

Preferred ranges for the novel terpolymer are from 25 to 40% by weight of vinylpyrrolidone, from 40 to 70% by weight of tert-butyl acrylate or tert-butyl methacrylate and from 5 to 10% by weight of acrylic acid of methacrylic acid.

Where the comonomer tert-butyl acrylate or methacrylate is used, the terpolymer obtained possesses optimum solubility, in particular in the alcohol/hydrocarbon propellant mixtures used in hair sprays, as well as optimum film-forming properties, which could not be foreseen, and meets the requirements set. This is particularly true since some of the copolymers with n-butyl and isobutyl acrylate and methacrylate have proven unsatisfactory in practical tests to determine their compatibility with propellant gases and curl retention.

The novel terpolymers are useful as film formers, in particular for hair sprays, but may also be used in hair-setting compositions, hair foams or hair gels.

The novel terpolymers are advantageously in a form which is partly or completely neutralized by an organic amine, from 5 to 100%, preferably from 50 to 90%, of the carboxyl groups being neutralized. The carboxyl groups are preferably neutralized with an alkanolamine from the series consisting of the mono-, di- and trialkanolamines where the alkanol radical is of 2 to 5 carbon atoms, such as mono-, di- or triethanolamine, mono-, di- or tripropanolamine or 2-amino-2-methylpropanol, or an alkanediolamine where the alkanediol radical is of 2 to 4 carbon atoms, such as 2-amino-2-methylpropane-1,3-diol or 2-amino-2-ethylpropane-1,3-diol, or by di(methoxyethyl)-amine or a primary, secondary or tertiary alkylamine having a total of 5 to 10 carbon atoms, such as N,N-diethylpropylamine.

2-amino-2-methylpropanol, triisopropanolamine and 2-amino-2-ethylpropane-1,3-diol are preferred.

The present invention furthermore relates to a hair treatment agent which contains, as a film former, a novel terpolymer in the partly or completely neutralized form, in an amount of from 0.5 to 15, preferably from 1 to 10, %, based on the total weight, and the use of the novel terpolymers in hair treatment agents.

The particularly preferred formulation is a hair spray composition which contains from 0.5 to 15% by weight of a novel terpolymer, from 5 to 100%, preferably from 50 to 90%, of whose carboxyl groups have been neutral with one of the abovementioned organic amines, from 10 to 95% by weight of a solvent selected from the group consisting of acetone, ethanol, propanol, isopropanol, 1-methoxypropan-2-ol and mixtures of these, and from 5 to 90% by weight of a propellant selected from the group consisting of propane, n-butane, isobutane, 2,2-dimethylpropane, isopentane, dimethyl ether and mixtures of these.

This hair spray composition may also contain from 0.1 to 5% by weight of water or from 1 to 35% by weight of methylene chloride or trichloromethane, the percentages being based on the total weight.

The preferred compositions contain
from 1 to 10% by weight of a resin according to the invention,
from 15 to 60% by weight of a solvent and
from 40 to 85% by weight of propellant gas.

The novel terpolymers of the compositions stated above and described in detail in the Examples are advantageously and preferably used in hair sprays of the above general formulation.

If importance is attached to a particularly good hair setting composition, terpolymers which contain methacrylic acid and at the same time are the most compatible with propellant gas are recommended.

In addition, the water solubility of the terpolymers used may play an important role in formulations which contain water as a solvent. Such formulations are, in particular, hair setting compositions, hair foams and hair gels. For such purposes, it is advisable to use fairly high vinylpyrrolidone and acrylic acid or methacrylic acid contents within the stated ranges, for example as in Examples 1 to 9.

An advantageous formulation for hair setting compositions contains
from 1 to 15% by weight of a novel terpolymer, from 5 to 100%, preferably from 50 to 90%, of whose carboxyl groups have been neutralized by one of the abovementioned organic amines,
from 0 to 99% by weight of a solvent selected from the group consisting of acetone, ethanol (96% pure), propanol, isopropanol, 1-methoxypropan-2-ol and mixtures of these, and
from 0 to 99% by weight of water.

A preferred hair setting composition is predominantly aqueous and contains from 2 to 10% by weight of the terpolymer defined above and from 60 to 98% by weight of water and, where relevant, one of the abovementioned solvents or mixtures of these to make up to 100% by weight. The preparation of aqueous formulations is a particular advantage of the present invention.

An advantageous composition for hair foams consists of
from 1 to 15, preferably from 5 to 10, % by weight of a novel terpolymer, from 5 to 100%, preferably from 50 to 90%, of whose carboxyl groups have been neutralized by one of the abovementioned amines,
from 5 to 90, preferably from 60 to 80, % of weight of water,
from 0 to 15, preferably from 5 to 10, % by weight of a solvent from the group consisting of acetone, ethanol, propanol, isopropanol, 1-methoxypropan-2-ol and mixtures of these, and
from 50 to 20% by weight of a propellant selected from the group consisting of propane, n-butane, isobutane, 2,2-dimethylpropane, isopentane, dimethyl ether and mixtures of these, 25:75 propane/butane mixtures being preferred.

From 0.5 to 1% by weight, based on the total weight, of foam-forming and foam-stabilizing assistants familiar to the skilled worker are added to these compositions. Examples, are Ceteareth 25 or 11, Nonoxynol 14 or 10 and Cocamide DEA (cf. CTFA, Cosmetics Ingredient Dictionary, 3rd edition 1982).

Of course, conventional additives, such as perfume, preservatives, etc., are also suitable for the various abovementioned types of formulation.

This shows that aqueous hair treatment agents constitute a preferred subject of the present invention. Particularly suitable for aqueous hair formulations are the terpolymers composed of vinylpyrrolidone, tert-butyl acrylate and methacrylic acid, these terpolymers being used in an amount from 2 to 10% by weight, based on the total weight.

The novel copolymers are prepared by conventional free radical copolymerization, preferably by solution polymerization in a monohydric lower alcohol of 1 to 4 carbon atoms, in particular ethanol or isopropanol. The conventional peroxides, such as benzoyl peroxide, tert-butyl perpivalate, tert-butyl per-2-ethylhexanoate, di-tert-butyl peroxide or tert-butyl hydroperoxide and azo initiators, such as azobisisobutyronitrile, are used as initiators, advantageously in amounts of from 0.3 to 2.0% by weight, based on the weight of the monomers.

After the polymerization, from 30 to 80% strength by weight solutions are generally obtained. If necessary, the solvent can be removed in a conventional manner, for example by spray-drying.

The novel terpolymers have K values of from 10 to 60, preferably from 15 to 50, measured in 2% strength by weight solution in ethanol at 25° C. in the acid form. The K value is a measure of the molecular weight (Fikentscher, Cellulosechemie 13 (1932), 58–64 and 71–74).

The Examples which follow illustrate the invention. Parts and percentages are by weight.

PREPARATION METHOD FOR EXAMPLES 1 AND 2 AND COMPARISON EXAMPLES 3 TO 8:

100 parts of a monomer mixture having the composition shown in the Examples in Table 1 are dissolved in 77 parts of isopropanol. 10% by weight of this monomer solution and 10% by weight of the prepared initiator solution consisting of 0.8 part of tert-butyl perpivalate and 12 parts of isopropanol are initially taken and heated to about 75° C. in a stirred flask equipped with a reflux condenser and two dropping funnels.

After initial polymerization, which is detectable in an increase in viscosity, the remaining monomer solution is added in the course of about 5 hours and at the same time the remaining initiator solution is introduced in the course of about 7 hours, the internal temperature being kept at about 80°–82° C. with gentle boiling. When the addition is complete, polymerization is continued for about 1 hour at these temperatures.

EXAMPLES 9 TO 12

100 parts of a monomer mixture of the composition shown in Examples 9 to 12 in Table 2 are dissolved in 24 parts of ethanol. 10% by weight of this monomer solution, 10% by weight of the prepared initiator solution consisting of 0.8 part of tert-butyl perpivalate and 27 parts of ethanol, and 50 parts of ethanol are initially taken and heated to about 75° C. in a stirred flask equipped with a reflux condenser and two dropping funnels.

After initial polymerization, which is detectable from an increase in viscosity, the remaining monomer solution is added in the course of 3 hours and at the same time the remaining initiator solution is introduced in the course of about 6 hours, the internal temperature being kept at about 78°–80° C.

When the addition is complete, polymerization is continued for about 1 hour at these temperatures.

COMPARATIVE EXAMPLES 3 TO 8

For comparison, terpolymers with n-, sec- and isobutyl acrylate and n-, sec- and isobutyl methacrylate are prepared under the conditions of Example 1, these terpolymers being shown in the Table and described in U.S. Pat. No. 3,405,084.

The compatibility with propellant gas and the curl retention are determined with the various terpolymers, 75% of whose carboxyl groups have been neutralized with 2-amino-2-methylpropanol. The results are summarized in Tables 1 and 2.

The compatibility with the propellant mixture propane/butane in a weight ratio of 40:60 indicates the amount, in % by weight, of this propellant mixture which can be used in an ethanolic hair spray solution containing 3% by weight of terpolymer and having a degree of neutralization of 75%, in order for the solution obtained still to be clear at 0° C. A compatibility of, for example, 71% with propellant gas means that a 3% strength by weight solution containing 71% by weight of propellant gas, the remainder to 100% by weight being ethanol, gives a clear solution at 0° C.

The curl retention is a measure of the hair setting effect. It is measured in a model experiment using curls produced by a conventional water wave in hair about 15 cm long which has been sprayed for 4 seconds from a distance of 10 cm with 2% strength by weight spray solution containing a resin shown in Table 1 or 2 and having a degree of neutralization of 75%. After the suspended curls have been treated for 5 hours in a conditioned chamber (25° C., 90% relative humidity), the relative deformation (extension) of the curls, based on the original shape, is determined. A high value indicates a good setting effect, ie. 100% would denote retention of the original shape of the suspended curls while 0% would represent fully extended hair.

The results show that the novel terpolymers have superior properties in the combination of compatibility with propellant gas and hair setting effect.

As a rule, propellant gas compatibilities of less than 60% and a curl retention of less than 50% are not sufficient in practice. Hence, in spite of having good curl retention, Comparative Example 8 is not recommended. Comparative Example 7 is at the lower limit of usefulness. It was not expected that the novel terpolymers with tert-butyl acrylate and tert-butyl methacrylate would give the best values in the combination of the properties investigated. The compositions in which acrylic acid is replaced with methacrylic acid give even better results. Examples of formulations:

EXAMPLE 13

Aerosol hair spray

Polymer according to Example 11: 2.0%
2-Amino-2-methylpropanol: 0.04%
Propane/butane (15:85): 65.0%
Ethanol, anhydrous: 32.96%
Perfume oil: q.s.

EXAMPLE 14

Hair setting composition, purely aqueous

Polymer according to Example 9: 4.0%
2-Amino-2-methylpropanol: 0.18%
Distilled water: 95.82%
Perfume oil: q.s.

EXAMPLE 15

Hair setting composition, aqueous alcoholic

Polymer according to Example 9: 4.0%
2-Amino-2-methylpropanol: 0.18%
Ethanol: 33.82%
Water: 62.0%
We claim:

TABLE 1

| | Composition (% by weight) | Compatibility with propellant gas (40:60 propane/butane, in absolute ethanol 0° C.) | Curl retention (25° C., 90% rel. humidity, 5 h) | K value (2% strength by weight in ethanol, 25° C.) |
|---|---|---|---|---|
| Example no. | | | | |
| 1. | 40 VP/50 tert.-BA/10 AA | 71% | 56% | 20 |
| 2. | 40 VP/50 tert.-BMA/10 AA | 64% | 75% | 22 |
| Comparative Example no. | | | | |
| 3. | 40 VP/50 n-BA/10 AA | 65% | 29% | 20 |
| 4. | 40 VP/50 sec.-BA/10 AA | 68% | 24% | 19 |
| 5. | 40 VP/50 iso-BA/10 AA | 68% | 27% | 19 |
| 6. | 40 VP/50 n-BMA/10 AA | 58% | 57% | 22 |
| 7. | 40 VP/50 sec.-BMA/10 AA | 61% | 54% | 22 |
| 8. | 40 VP/50 iso-BMA/10 AA | 59% | 67% | 22 |

VP N—vinylpyrrolidone, BA butyl acrylate, BMA butyl methacrylate, AA acrylic acid

TABLE 2

| | Composition (% by weight) | Compatibility with propellant gas (40:60 propane/butane, in absolute ethanol 0° C.) | Curl retention (25° C., 90% rel. humidity, 5 h) | K value (2% strength by weight in ethanol, 25° C.) |
|---|---|---|---|---|
| Example no. | | | | |
| 9. | 40 VP/50 tert.-BA/10 MAA | 68% | 83% | 30 |
| 10. | 38 VP/60 tert.-BA/2 MAA | 79% | 83% | 25 |
| 11. | 25 VP/70 tert.-BA/5 MAA | 77% | 86% | 24 |
| 12. | 20 VP/70 tert.-BA/10 MAA | 70% | 88% | 27 |

VP N—vinylpyrrolidone, BA butyl acrylate, BMA butyl methacrylate, MAA methacrylic acid 1. A terpolymer which is obtained by free radical polymerization of a monomer mixture consisting of
   from 20 to 50% by weight vinylpyrrolidone,
   from 40 to 70% by weight of t-butyl acrylate or t-butyl methacrylate, and
   from 2–15% by weight of acrylic acid or methacrylic acid and, if necessary, from 5 to 100% of whose carboxyl groups have been neutralized by an organic amine and which has a K value of from 10–60, said terpolymer being capable of being formulated as a hairspray formulation which has a propellant gas compatibility of at least 60% and a curl retention of at least 50%.

2. The terpolymer as claimed in claim 1, which is obtained by free radical polymerization of
   from 20 to 40% by weight of vinylpyrrolidone,
   from 40 to 70% by weight of tert-butyl acrylate or tert-butyl methacrylate and
   from 5 to 10% by weight of acrylic acid or methacrylic acid and
   from 50 to 90% of whose carboxyl groups have been neutralized with an organic amine.

3. An aqueous hair treatment agent containing, as a film former, a terpolymer as claimed in claim 1, of vinylpyrrolidone, tert-butyl acrylate and methacrylic acid, in an amount of from 2 to 10% by weight, based on the total weight.

4. A hair treatment agent comprising, from 0.5 to 15% by weight, based on the total weight of the agent, of a terpolymer prepared by polymerizing from 20 to 50% by weight of vinypyrrolidone, from 40–70% by weight of t-butyl acrylate or t-butyl methacrylate and from 2–15% by weight of acrylic acid or methacrylic acid and, if necessary, from 5–100% of whose carboxyl groups have been neutralized by an organic amine and which has a K value of from 10–60.

5. A hair spray formulation, comprising:
   from 0.5–15% by weight of a film forming terpolymer prepared by polymerizing from 20–50% by weight by weight of vinylpyrrolidone, from 40–70% by weight of t-butyl acrylate or t-butyl methacrylate and from 2–15% by weight of acrylic cid or methacrylic acid and, if necessary, from 5–100% of whose carboxyl groups have been neutralized by an organic amine and which has a K value of from 10–60;
   from 10–95% by weight of a solvent selected from the group consisting of acetone, ethanol, propanol, isopropanol, 1-methoxypropanol and mixtures thereof, and
   from 5–90% by weight of a propellant selected from the group consisting of propane, n-butane, isobutane, 2,2-dimethylpropane, isopentane, dimethyl ether and mixtures thereof.

* * * * *